US010265342B2

(12) United States Patent
Sung et al.

(10) Patent No.: US 10,265,342 B2
(45) Date of Patent: Apr. 23, 2019

(54) SUSTAINED-RELEASE COMPOSITION, METHOD FOR FABRICATING, AND USE THEREOF

(71) Applicant: NATIONAL TSING HUA UNIVERSITY, Hsinchu (TW)

(72) Inventors: Hsing-Wen Sung, Hsinchu (TW); Chieh-Cheng Huang, Taoyuan (TW); Wei-Lin Wan, Hsinchu County (TW); Meng-Hsuan Hsieh, Hsinchu (TW); Po-Chien Shih, Taichung (TW); Hsin-Yi Hu, Tainan (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 15/672,280

(22) Filed: Aug. 8, 2017

(65) Prior Publication Data
US 2018/0333431 A1   Nov. 22, 2018

(30) Foreign Application Priority Data

May 16, 2017   (TW) .............................. 106116146 A (51) Int. Cl.
| *A61K 33/06* | (2006.01) |
| *A61K 31/10* | (2006.01) |
| *A61K 9/14* | (2006.01) |
| *A61K 9/107* | (2006.01) |

(52) U.S. Cl.
CPC .............. *A61K 33/06* (2013.01); *A61K 9/107* (2013.01); *A61K 9/146* (2013.01); *A61K 31/10* (2013.01)

(58) Field of Classification Search
None
See application file for complete search history.

(56) References Cited

U.S. PATENT DOCUMENTS

2002/0044978 A1* 4/2002 Cheon .................... A61K 31/10
424/754

FOREIGN PATENT DOCUMENTS

| CN | 103966680 A | 8/2014 |
| CN | 106236699 A | 12/2016 |

OTHER PUBLICATIONS

Fahmy (Fabrication of Garlic Composites Nano-biotics and Investigating their Anti-bacterial Activities. (2015)).*
Tyler Richard Long, "Synthesis of polymers with the potential to release H2S: polydicyclopentadiene nanoporous membranes", 2014, Thesis, The University of Iowa, United States.
S.C. Cifuentes et al., "In vitro degradation of biodegradable polylactic acid/magnesium composites: Relevance of Mg particle shape", Acta Biomaterialia, published on Mar. 1, 2016, vol. 32, pp. 348-357, published by Elsevier Ltd., Netherlands.

* cited by examiner

*Primary Examiner* — Jake M Vu
(74) *Attorney, Agent, or Firm* — CKC & Partners Co., LLC (57) ABSTRACT

A sustained-release composition is provided in the present disclosure for producing a therapeutic gas, such as hydrogen sulfide or hydrogen. The sustained-release composition includes a precursor and a carrier. The precursor is diallyl trisulfide or magnesium, and the carrier includes a poly lactic-co-glycolic acid copolymer for carrying the precursor with an efficient amount.

10 Claims, 11 Drawing Sheets

SUSTAINED-RELEASE COMPOSITION, METHOD FOR FABRICATING, AND USE THEREOF

RELATED APPLICATIONS

This application claims priority to Taiwan Application Serial Number 106116146, filed May 16, 2017, which is herein incorporated by reference.

BACKGROUND

Technical Field

The present disclosure relates to a sustained-release composition. More particularly, the present disclosure relates to a sustained-release composition, method for fabricating and use the same capable of producing a therapeutic gas continuously.

Description of Related Art

Reactive oxygen species (ROS), such as superoxide, peroxides and hydroxyl radical, are formed as a natural byproduct of the normal metabolism of oxygen. The ROS are highly reactive due to their free electrons and have important roles in cell signaling and homeostasis. However, excessive ROS, which are produced in response to the inflammation, will result in oxidative stress.

Ischemia diseases, such as critical limb ischemic (CLI), are caused by insufficient blood perfusion and will further lead to tissue hypoxia and necrosis. In the inflammatory environment in ischemic tissues, neutrophils, monocytes and macrophage will produce a large amount of ROS, thus generating the oxidative stress.

In addition to nitric oxide (NO) and carbon oxide (CO), hydrogen sulfide ($H_2S$) is recognized as a gaseous signaling molecule and can be endogenously produced in a variety of tissues and cells of mammals. Recently, hydrogen sulfide with a physiological concentration can reduce the level of oxidative stress through direct scavenging ROS or indirectly inducing the expression of antioxidant genes. Polysulfides, such as diallyl trisulfide (DATS), are common hydrogen sulfide precursors that are relatively stable compared to other common precursors such as sodium sulfide ($Na_2S$) or sodium hydrosulfide (NaHS). However, the half-life of the diallyl trisulfide in aqueous solution is only around 15 minutes. Hence, the half-life of the diallyl trisulfide is too short to provide a long-term therapeutic effect.

In addition, hydrogen is also recognized as a therapeutic gas for selectively scavenging the ROS and reducing the oxidative stress. In particular, magnesium (Mg) can be employed as a hydrogen precursor and react with water to produce magnesium hydroxide precipitate and hydrogen molecules. The reaction as mentioned above is performed according to the formula (1):

$$Mg + 2H_2O \rightarrow Mg(OH)_2 + H_2 (g) \qquad (1).$$

However, the reaction rate is too fast to provide sufficient hydrogen at a lesion zone for a prolonged duration. Therefore, a long-term therapeutic effect also cannot be achieved.

SUMMARY

The present disclosure provides a sustained-release composition for producing a therapeutic gas. The sustained-release composition includes a precursor and a carrier. The precursor is diallyl trisulfide or magnesium, and the carrier includes a poly lactic-co-glycolic acid (PLGA) copolymer for carrying the precursor with an efficient amount.

The present disclosure further provides a method for fabricating the abovementioned sustained-release composition. The method includes providing a first solution, providing a second solution, performing a single emulsification and collecting the sustained-release composition. In the step of providing the first solution, the first solution is provided as an oil phase and includes the poly lactic-co-glycolic acid copolymer, the precursor and a solvent. In the step of providing the second solution, the second solution is provided as a water phase. The step of performing the single emulsification is achieved by mixing the first solution and the second solution to form the sustained-release composition.

The present disclosure further provides a method for treating indications for hydrogen sulfide therapy or hydrogen therapy. The method includes administering an effective amount of the abovementioned sustained-release composition to a subject suffered from the indications for hydrogen sulfide therapy or hydrogen therapy.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
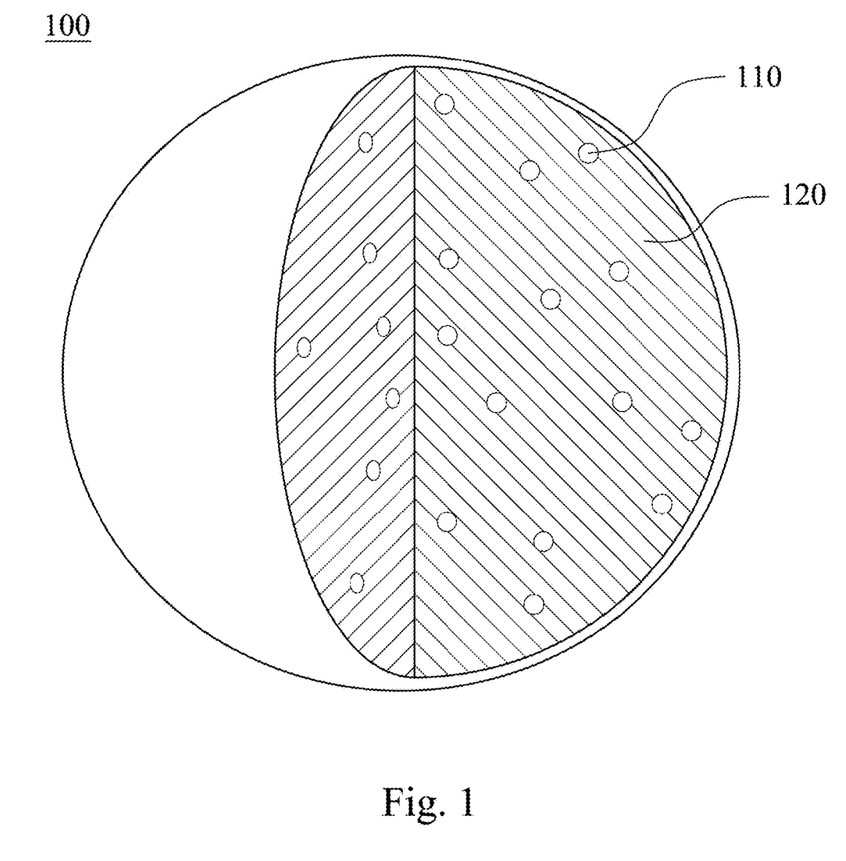
FIG. 1 is a structural schematic view showing a sustained-release composition according to the present disclosure.

Please refer to FIG. 1, which is a structural schematic view showing a sustained-release composition 100 according to the present disclosure. As shown in FIG. 1, the sustained-release composition 100 can be a microsphere and include a precursor 110 and a carrier 120. In particular, the carrier 120 is provided for carrying the precursor 110, and the precursor 110 is preferably evenly dispersed in the carrier 120.

The precursor 110 can be diallyl trisulfide. Thus, the sustained-release composition can release the diallyl trisulfide slowly so as to produce hydrogen sulfide slowly and continuously. Alternatively, the precursor 110 can be magnesium. Thus, the sustained-release composition can slow down the contact between the magnesium and water in the following application so as to produce the hydrogen continuously.

The carrier 120 includes a poly lactic-co-glycolic acid copolymer. In details, the poly lactic-co-glycolic acid copolymer is a copolymer composed of polylactic acid and polyglycolic acid and has a good biocompatibility. Thus, there are no adverse effects for human bodies when the sustained-release composition 100 of the present disclosure is applied for a subject suffered from the indications for hydrogen sulfide therapy or hydrogen therapy. Preferably, a copolymerization ratio of polylactic acid in the poly lactic-co-glycolic acid copolymer can range from 50 wt % to 80 wt %, and a copolymerization ratio of polyglycolic acid in the poly lactic-co-glycolic acid copolymer can range from 20 wt % to 50 wt %.

The size of the microsphere will influence the release rate of the precursor. The larger the size of the microsphere is, the slower the release rate of the precursor is. Accordingly, the sustained-release composition can be fabricated through the emulsification by homogenization to be a microsphere with an average particle size of 1 μm~10 μm. Alternatively, the sustained-release composition can be fabricated through the emulsification by a microfluidic system to be a microsphere with an average particle size of 10 μm~300 μm. That is, an average particle size of the microspheres in the present disclosure ranges from 0.2 μm to 300 μm.

When the precursor is the diallyl trisulfide, the sustained-release composition contains 1 wt % to 30 wt % of the diallyl trisulfide based on the total weight of the sustained-release composition. When the precursor is the magnesium, the sustained-release composition contains 1 wt % to 50 wt % of the magnesium based on the total weight of the sustained-release composition.

Figure 2:
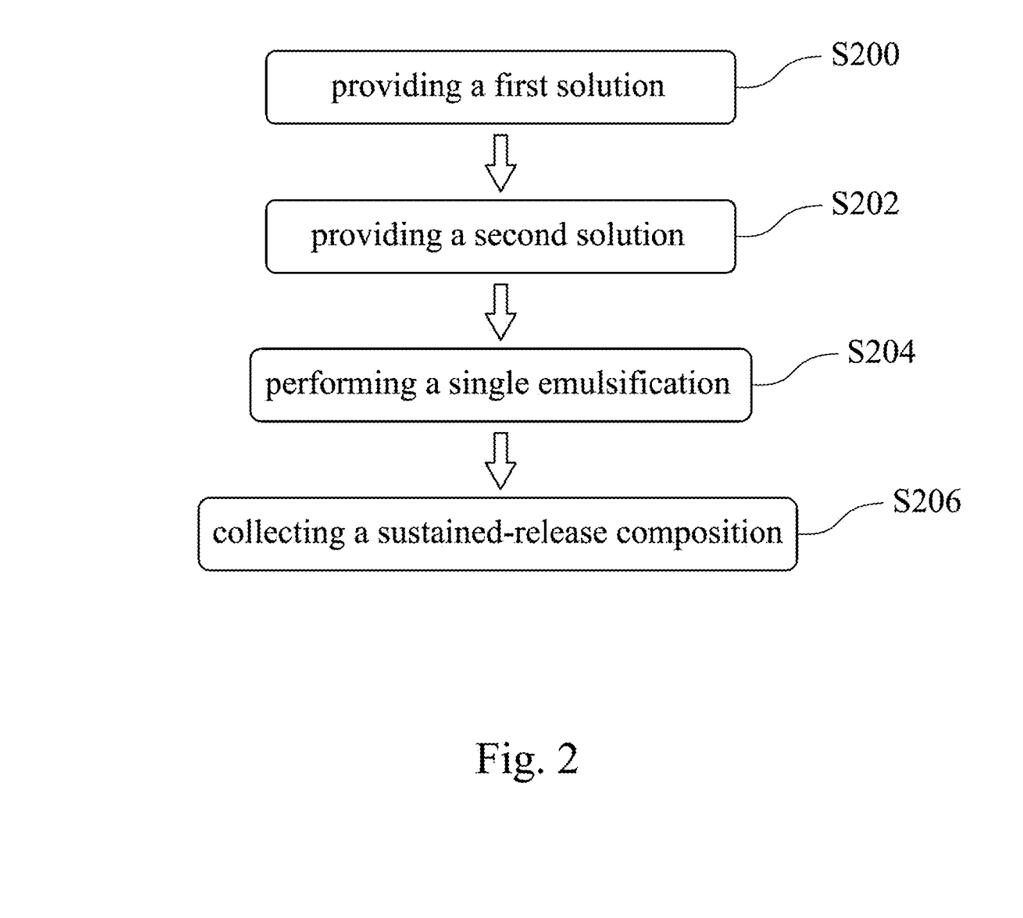
FIG. 2 is a flow chart showing a method for fabricating a sustained-release composition according to the present disclosure.

Please refer to FIG. 2, which is a flow chart showing a method for fabricating a sustained-release composition according to the present disclosure. The method includes Step S200, Step S202, Step S204 and Step S206.

In Step S200, a first solution is provided as an oil phase. A second solution is then provided as a water phase in Step S202. The first solution includes a poly lactic-co-glycolic acid copolymer, a precursor and a solvent. In particular, the solvent is provided for dissolving the poly lactic-co-glycolic acid copolymer and the precursor so that the solvent can be but not limited to dichloromethane, trichloromethane or ethyl acetate.

In Step S204, a single emulsification is performed. In details, the first solution and the second solution are mixed to perform the single emulsification for forming the sustained-release composition. More particularly, a mixing ratio of a volume of the first solution to a volume of the second solution ranges from 1:1 to 1:12 in the step of performing the single emulsification.

In Step S206, the sustained-release composition can be collected by steps of concentrating under reduced pressure, centrifuging, filtering, washing and drying.

Accordingly, the sustained-release composition, which is fabricated from the above-mentioned steps, can be utilized as one of drug ingredients for treating indications for hydrogen sulfide therapy or hydrogen therapy. In particular, the indications for hydrogen sulfide therapy or hydrogen therapy can be ischemia disorders or inflammation-related diseases (for example, arthritis). Furthermore, the drug can include a pharmaceutically acceptable salt.

The sustained-release composition has been described as mentioned above. In the following, a 1st embodiments and a 2nd embodiment will be further provided to illustrate the above-mentioned sustained-release composition and the method for fabricating thereof. The accompanied effects of the sustained-release compositions, respectively, disclosed in the 1st embodiment and the 2nd embodiment for promoting angiogenesis in ischemic tissues or cleaning ROS are evaluated through an animal model and an in vitro cell model. However, the present disclosure is not limited thereto.

Sustained-Release Composition and Method for Fabricating Thereof

1st Embodiment

In the 1st embodiment, 300 mg of the poly lactic-co-glycolic acid copolymer is dissolved in 10 mL of dichloromethane to form a solution containing the poly lactic-co-glycolic acid copolymer. Then, 20 μL of the diallyl trisulfide is added into 1 mL of the abovementioned solution to form the first solution. Alternatively, the poly lactic-co-glycolic acid copolymer and the diallyl trisulfide can be added into the dichloromethane at the same time for forming the first solution.

In particular, a copolymerization ratio of polylactic acid in the poly lactic-co-glycolic acid copolymer is 75 wt %, and a copolymerization ratio of polyglycolic acid in the poly lactic-co-glycolic acid copolymer is 25 wt %. More particularly, an inherent viscosity (IV) of the poly lactic-co-glycolic acid copolymer is 0.17 dL/g.

In the 1st embodiment, the second solution is a solution containing polyvinyl alcohol, which is used as a surfactant. Thus, a solution containing other surfactants, such as sodium lauryl sulfate, dimethylaminoborane, or a polyoxyethylene-polyoxypropylene block copolymer is also available in the present disclosure. The first solution, which is used as art oil phase, and the second solution, which is used as a water phase, are mixed by a volume ratio of 1:3 and shocked by a homogenizer (POLYTRON® PT 1200 E) for 5 minutes to perform a single emulsification. Then, a sustained-release composition is obtained. That is, the poly lactic-co-glycolic acid copolymer is used as a carrier in the sustained-release composition of the 1st embodiment for carrying the diallyl trisulfide with an efficient amount so as to produce hydrogen sulfide continuously in the following application.

After the abovementioned steps, the sustained-release composition does not be separated from the dichloromethane. The dichloromethane is then removed under reduced pressure for 1 hour using a rotary evaporator (EYELA N-1200A). The sustained-release composition is collected by centrifuging and then washed by deionized water for three times to remove the remained polyvinyl alcohol.

In addition, the temperature of the solution will be raised when the single emulsification is performed by homogenizing. However, the dichloromethane is a volatile organic solvent and easy to be volatilized during the single emulsification. Thus, the single emulsification can be performed in an ice bath. The poly lactic-co-glycolic acid copolymer and the diallyl trisulfide are unstable under room temperature or a higher temperature so that the step of collecting the sustained-release composition is also performed in the ice bath.

The sustained-release composition collected by the abovementioned steps can be further dried and stored for the following analysis and application.

Figure 3A:
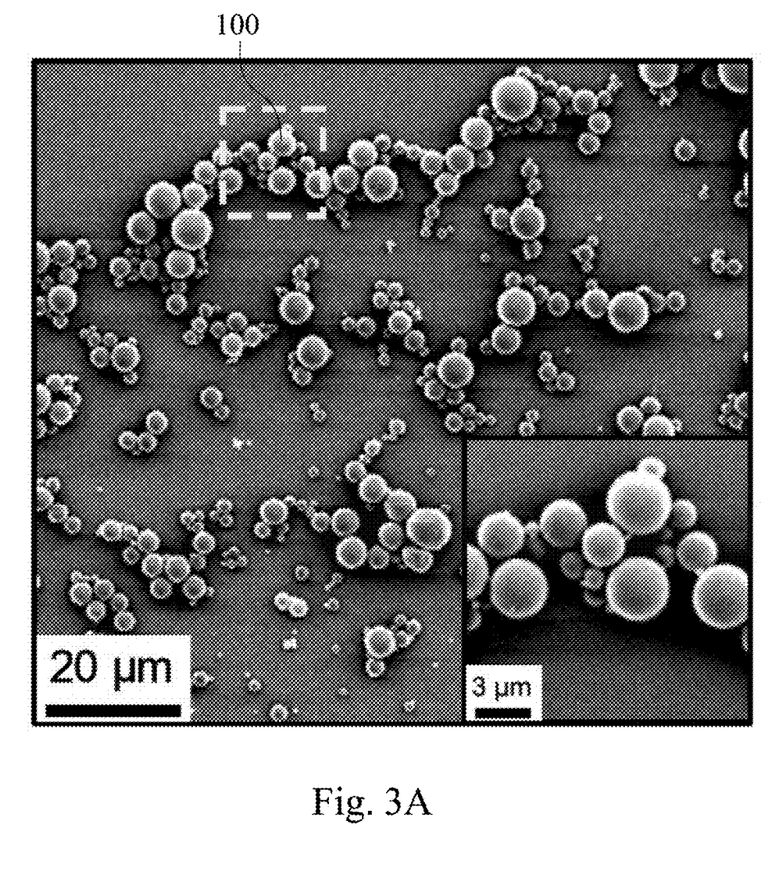
FIG. 3A is a scanning electron microscope image showing sustained-release compositions according to a 1st embodiment of the present disclosure.
Figure 3B:
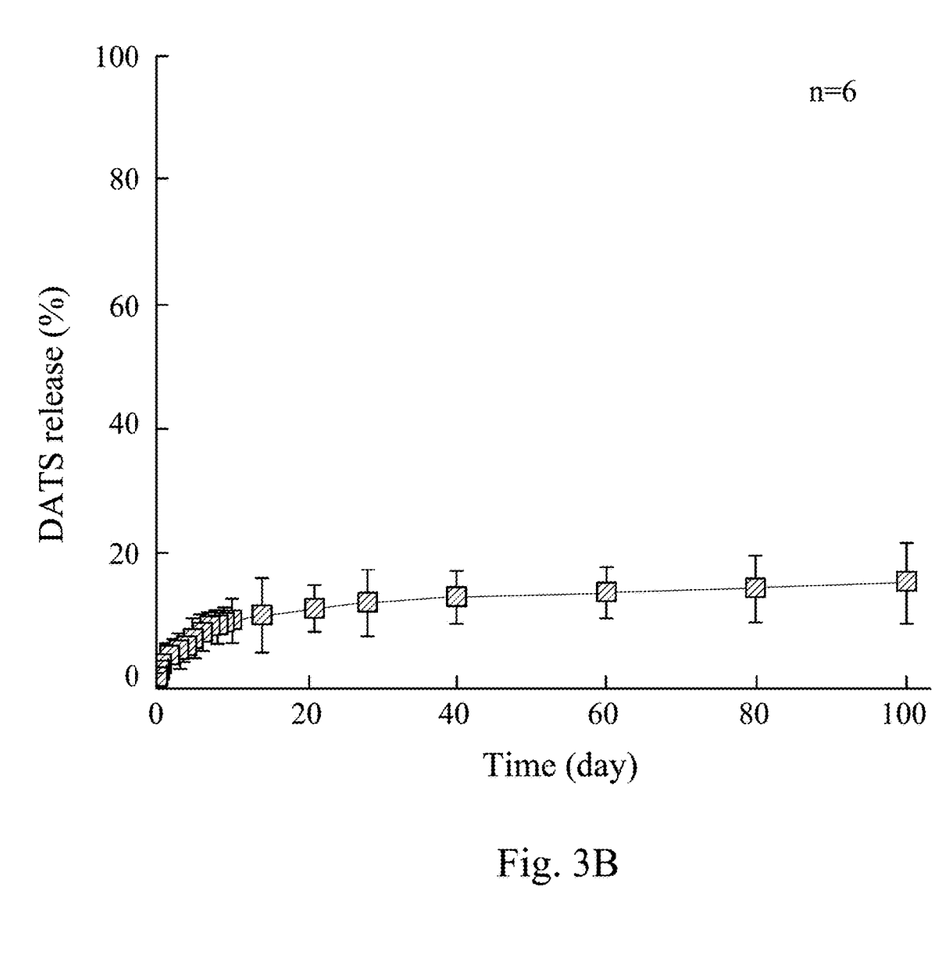
FIG. 3B is a relation between days of storage and diallyl trisulfide level of the sustained-release composition according to the 1st embodiment of the present disclosure.

Please refer to FIG. 3A and FIG. 3B. FIG. 3A is a scanning electron microscope image showing sustained-release compositions according to the 1st embodiment of the present disclosure, and FIG. 3B a relation between days of storage and diallyl trisulfide level of the sustained-release composition according to the 1st embodiment of the present disclosure. As shown in FIG. 3A, the sustained-release composition is a microsphere with an average particle size of 2.9±0.8 μm. In the 1st embodiment, each microsphere (that is, each sustained-release composition) can contain 14.0%±0.9 wt % of the diallyl trisulfide based on the total weight of the sustained-release composition. When the sustained-release composition is stored in a freezer, the diallyl trisulfide level of the sustained-release composition is kept around 20% as shown in FIG. 3B. That is, the sustained-release composition of the present disclosure can be stored for at least 14 weeks under the above-mentioned condition.

A releasing profile of the diallyl trisulfide of the sustained-release composition is further evaluated under an environment temperature of 37° C. at pH values of 7.4 and 6.5, separately. Please refer to FIG. 4, which is a release profile of diallyl trisulfide from the sustained-release composition according to the 1st embodiment of the present disclosure. The amount of the released diallyl trisulfide is calculated by measuring the amount of the diallyl trisulfide remained in the sustained-release composition. In short, the sustained-release composition, which is sampled at a specific point in time, is dissolved in dimethyl sulfoxide and then diluted to 10 times with acetonitrile. The content of the diallyl trisulfide of the sustained-release composition can be analyzed by a high performance liquid chromatography (HPLC). Thus, the remained content of the diallyl trisulfide can be evaluated.

Figure 4:
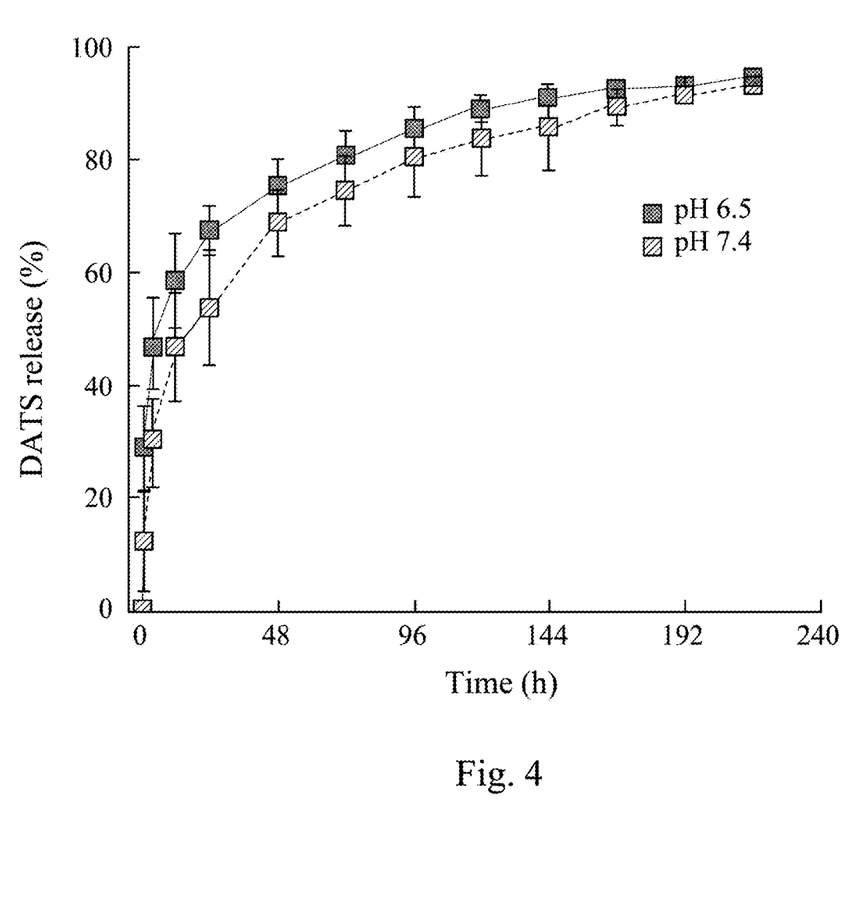
FIG. 4 is a release profile of diallyl trisulfide from the sustained-release composition according to the 1st embodiment of the present disclosure.

In FIG. 4, the release of the diallyl trisulfide of the sustained-release composition can be divided into two stages: the diallyl trisulfide is accumulated quickly in the first stage and released slowly and continuously in the second stage. When the sustained-release composition is applied for treating ischemic diseases, the concentration of the hydrogen sulfide in plasma can be raised quickly and accumulated. Then, the hydrogen sulfide can be released slowly and continuously for achieving a long-term therapeutic effect.

In details, the concentration of the diallyl trisulfide can be accumulated around 75% to 80% within 48 hours when the sustained-release composition is administered to an acidic environment. On the contrary, the accumulated amount, which is also accumulated within 48 hours, of the diallyl trisulfide is lower when the sustained-release composition is administered to a neutral environment. However, the sustained-release composition can release the diallyl trisulfide over one week no matter which environment the sustained-release composition is administered to.

2nd Embodiment

Figure 5:
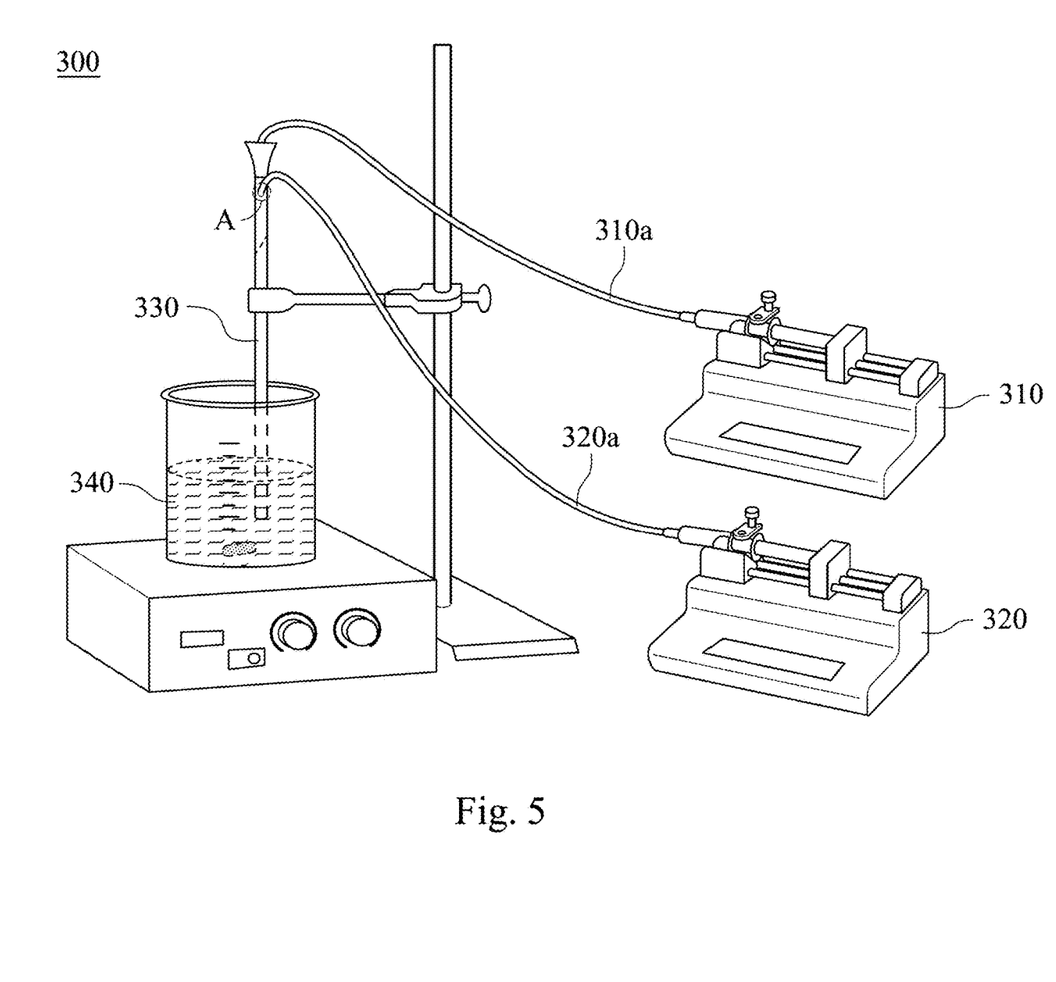
FIG. 5 is an operational schematic view showing a fabrication of sustained-release compositions according to a 2nd embodiment of the present disclosure.

Please refer to FIG. 5, which is an operational schematic view showing a fabrication of sustained-release compositions according to the 2nd embodiment of the present disclosure. As shown in FIG. 5, the method for fabricating the sustained-release composition of the 2nd embodiment is performed in a microfluidic system 300. The microfluidic system 300 includes a first infusion pump 310, a second infusion pump 320, a transmission unit 330, a collecting unit 340 and two tubes 310a, 320a for connecting the first infusion pump 310 and the second infusion pump 320, respectively, to the transmission unit 330.

In the 2nd embodiment, the transmission unit 330 is set up by polishing a 23 G needle and then embedding the 23 G needle into a glass capillary. Then, the first solution and the second solution are prepared separately. The first solution is provided as an oil phase, and the magnesium is dispersed in the poly lactic-co-glycolic acid copolymer by using the dichloromethane as the solvent. The second solution is provided as the water phase. In particular, the concentration of the poly lactic-co-glycolic acid copolymer in the first solution is 40 mg/mL, the concentration of the magnesium is 5 mg/mL, and the second solution is the solution containing 5 wt % of polyvinyl alcohol. More particularly, a particle size of the magnesium used in the 2nd embodiment is 20 μm. Moreover, a copolymerization ratio of polylactic acid in the poly lactic-co-glycolic acid copolymer is 75 wt %, and a copolymerization ratio of polyglycolic add in the poly lactic-co-glycolic acid copolymer is 25 wt %.

The first solution and the second solution are loaded into the tube 310a and the tube 320a, respectively, by the first infusion pump 310 and the second infusion pump 320. Then, the first solution and the second solution are mixed uniformly at an intersection A of the tube 310a and the tube 320a for forming the sustained-release compositions. The sustained-release compositions flow into the collecting unit 340 along the transmission unit 330 and placed in a hood (not shown in the figure) for volatilizing organic components. In particular, a flow rate of the first solution is 12 mL/h, and a flow rate of the second solution is 5 mL/min. More particularly, the other solution containing 5 wt % of polyvinyl alcohol can be loaded into the collecting unit 340 for collecting the sustained-release compositions. In the 2nd embodiment, each of the sustained-release compositions utilizes the poly lactic-co-glycolic acid copolymer as the carrier for carrying the magnesium with an effective amount so as to produce the hydrogen continuously in the following application.

A filter paper is finally provided to remove the polyvinyl alcohol solution and filter out the sustained-release compositions. The sustained-release compositions are washed repeatedly by the deionized water, frozen-dried at 80° C. and then stored for the following analysis and application.

Figure 6A:
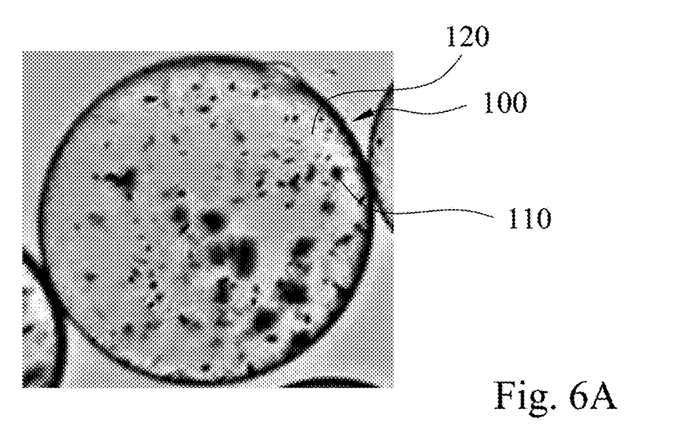
FIG. 6A is an optical microscope image of the sustained-release composition according to the 2nd embodiment of the present disclosure.
Figure 6B:
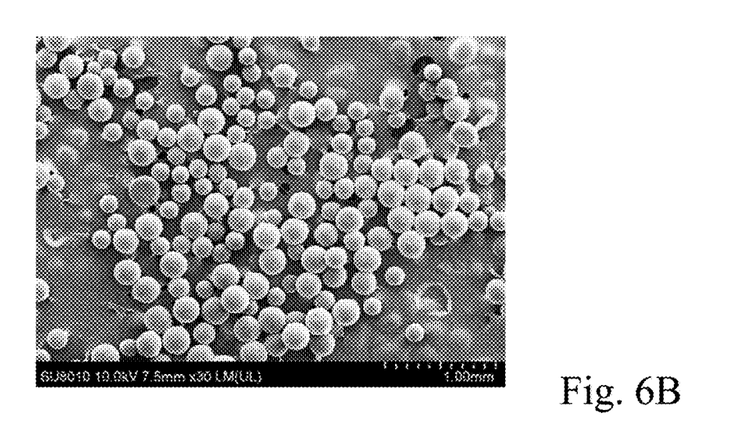
FIG. 6B is a low magnification scanning electron microscope image of the sustained-release composition according to the 2nd embodiment of the present disclosure.
Figure 6C:
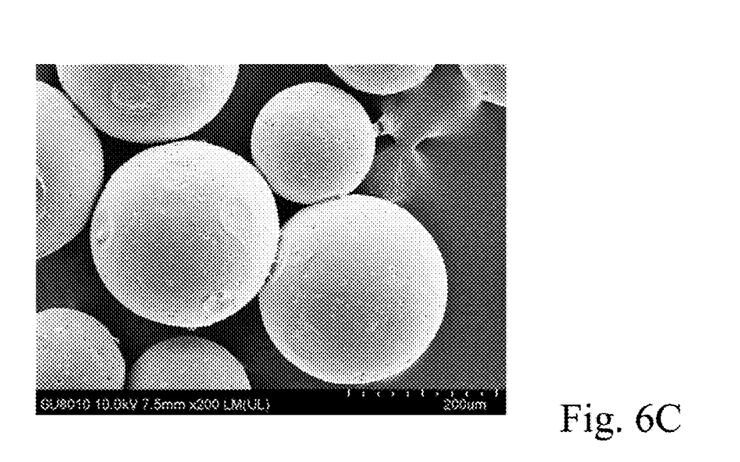
FIG. 6C is a high magnification scanning electron microscope image of the sustained-release composition according to the 2nd embodiment of the present disclosure.

Please refer to FIG. 6A, FIG. 6B and FIG. 6C. FIG. 6A is an optical microscope image of the sustained-release composition according to the 2nd embodiment of the present disclosure, FIG. 6B is a low magnification scanning electron microscope image of the sustained-release composition according to the 2nd embodiment of the present disclosure, and FIG. 6C is a high magnification scanning electron microscope image of the sustained-release composition according to the 2nd embodiment of the present disclosure. As shown in FIG. 6A, the sustained-release composition 100 is a microsphere. Moreover, the precursor, that is, the magnesium, capsuled by the carrier 120 can be observed clearly in FIG. 6A. An average particle size of the microsphere can be calculated from FIG. 6B and FIG. 6C and is 230±20 μm. In addition, each microsphere (that is, each of the sustained-release compositions of the 2nd embodiment) contains 10 wt % of the magnesium based on the total weight of the sustained-release composition.

Figure 7A:
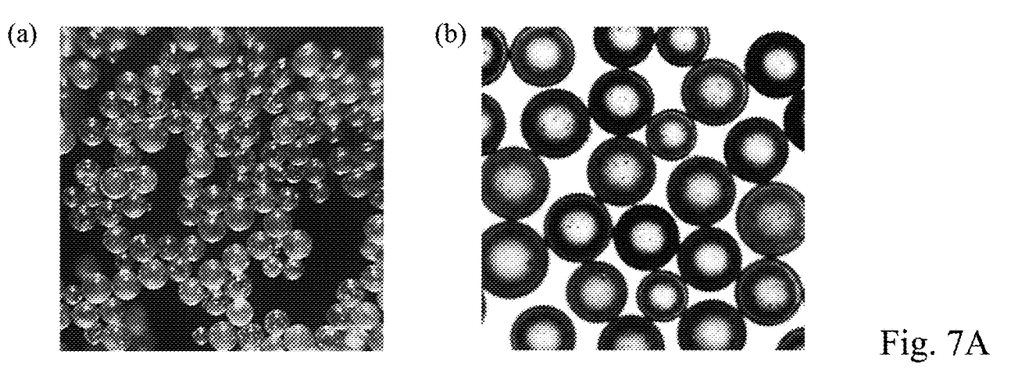
FIG. 7A are optical microscope images of poly lactic-co-glycolic acid microspheres obtained, respectively, using (a) a top light source and (b) a bottom light source.
Figure 7B:
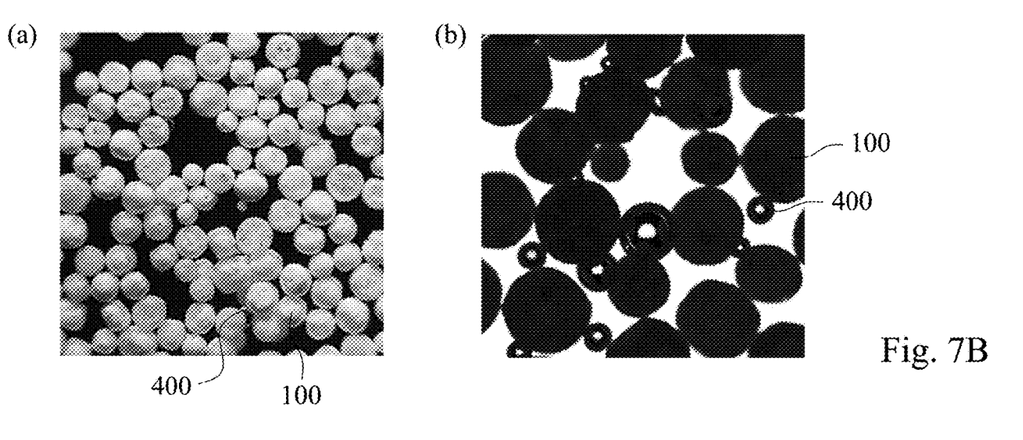
FIG. 7B are optical microscope images of the sustained-release composition obtained, respectively, using (a) a top light source and (b) a bottom light source.

Please refer to FIG. 7A and FIG. 7B. FIG. 7A are optical microscope images of poly lactic-co-glycolic acid microspheres obtained, respectively, using (a) a top light source and (b) a bottom light source, and FIG. 7B are optical microscope images of the sustained-release composition obtained, respectively, using (a) a top light source and (b) a bottom light source. In details, bubbles are not produced as shown in FIG. 7A when the poly lactic-co-glycolic acid microspheres, which do not carry the magnesium, are put into water. As shown in FIG. 7B, the hydrogen is produced according to the formula (1) when the sustained-release composition of the present disclosure is put into water. Thus, bubbles 400 can be observed around the sustained-release composition 100.

Figure 8:
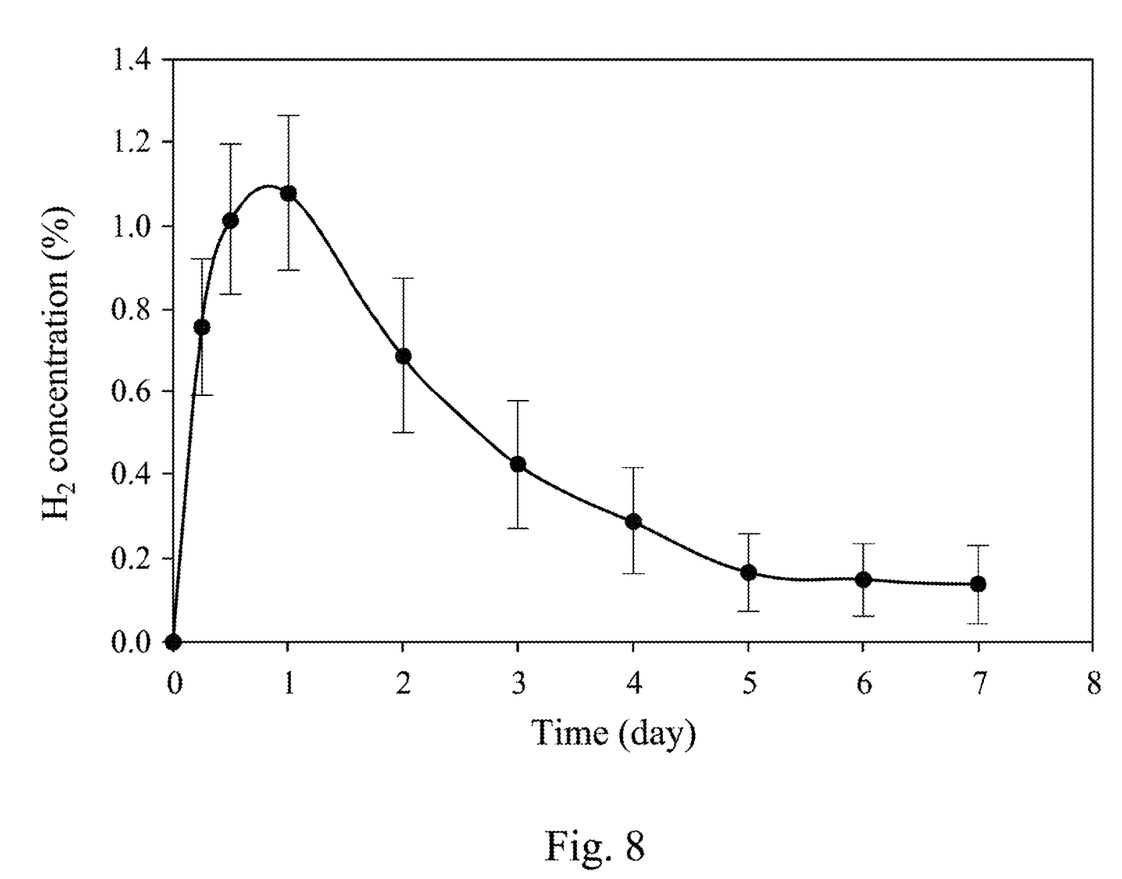
FIG. 8 is a release profile of hydrogen in the 2nd embodiment of the present disclosure.

In the present embodiment, a releasing profile of the hydrogen of the sustained-release composition is further evaluated under an environment temperature of 37° C. at pH values of 7.4. As shown in FIG. 8, the release of the hydrogen of the sustained-release composition of the 2nd embodiment can be divided into two stages: the hydrogen is accumulated quickly in the first stage and released slowly and continuously in the second stage for at least one week. When the sustained-release composition is applied for treating ischemic diseases, the concentration of the hydrogen in plasma can be raised quickly and accumulated. Then, the hydrogen can be released slowly and continuously for achieving a long-term therapeutic effect.

Use of Sustained-Release Composition—Animal Model

As mentioned above, the sustained-release composition can be applied for promoting angiogenesis in ischemic tissues. Thus, the effect of such the use will be further evaluated through a mouse hindlimb ischemia model and utilizes the sustained-release composition of the 1st embodiment of the present disclosure. In the present disclosure, all animal experimentation processes are performed according to an animal care and use guideline promulgated by Council of Agriculture, Executive Yuan, R.O.C. (Taiwan). In particular, BALB/c mice are served as a platform for developing the animal model. In the beginning, for each of the mice, 2 L/min of oxygen and 4% inhaled isoflurane are provided into an anesthesia box to introduce a general anesthesia in the mouse under room temperature, and the mouse is intubated and supplied by 3% isoflurane continuously. After a medial thigh area of the mouse is cut by a scalpel, the mouse is subjected by ligation of upper end and lower end of femoral artery to simulate hindlimb ischemia.

Subsequently, an intramuscular injection is performed into the quadriceps muscle adjacent to the proximal ligation site. The abovementioned mice can be divided into four groups according to the treatment. In details, the mice of Group 1 are only injected with physiological saline. The mice of Group 2 are injected with free diallyl trisulfide, which does not be carried by the carrier. The mice of Group 3 are injected with empty carriers, which do not contain the diallyl trisulfide. The mice of Group 4 are injected with the sustained-release composition of the 1st embodiment.

Figure 9:
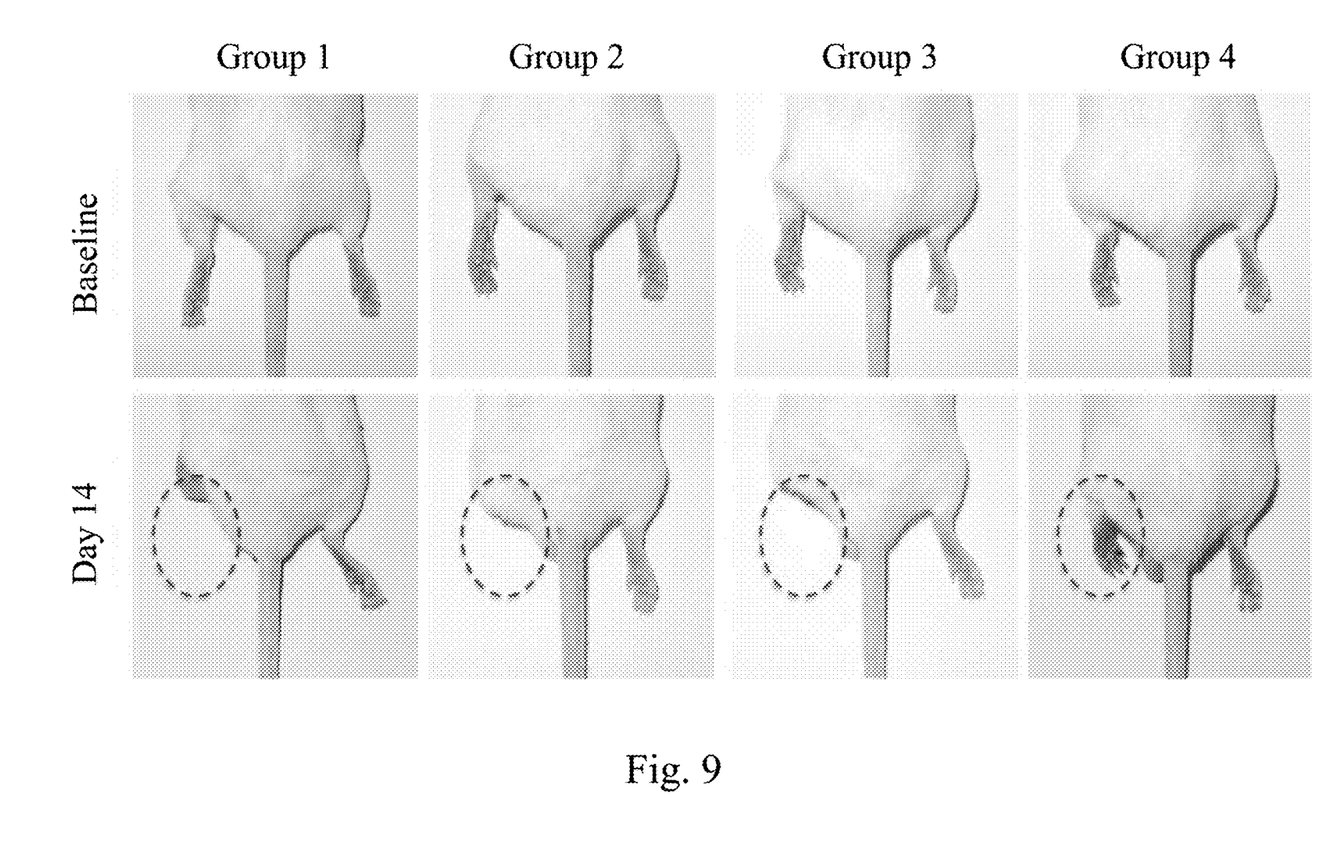
FIG. 9 shows appearances of hindlimbs of mice.

The supply of the anesthetic gas is reduced gradually, and the wounds of the mice are stitched. After completing the operation, the mice will be supplied with oxygen until the mice wake up. Please refer to FIG. 9, which shows limb appearances of the mice after fourteen days. As shown in FIG. 9, the muscle atrophies of the hindlimbs of the mice of Group 1 and Group 3 are obvious. After fourteen days, the mice of Group 1 and Group 3 even lose their hindlimbs. As to the mouse of Group 2, muscle atrophy of the hindlimb is slighter than that of the mice of Group 1 and Group 3 due to the hydrogen sulfide released by the free diallyl trisulfide. However, the half-life of the free diallyl trisulfide is too short to provide a long-term therapeutic effect. Thus, the mouse of Group 2 also lose its hindlimb after fourteen days.

Although the mouse of Group 4 is also suffered from slight muscle atrophy in its hindlimb, the sustained-release composition of the present disclosure can slowly and continuously release the diallyl trisulfide for producing the hydrogen sulfide continuously so as to promoting the angiogenesis around the ischemic tissues and mitigating the muscle atrophy of the hindlimb of the mouse. Thus, the mouse of Group 4 still keeps its hindlimb after fourteen days.

Use of Sustained-Release Composition—In Vitro Cell Model

Lipopolysaccharides (LPS) are glycolipids found in the outer membrane of some types of Gram-negative bacteria and can active many kinds of cells, such as macrophage or microglia, to release ROS or inflammatory precursors, such as TNF-α or IL-1β. Thus, an in vitro cell model is constructed herein by using the lipopolysaccharide to active the macrophage for producing the ROS. A staining reagent, that is, 2', 7'-Dichlorofluorescein diacetate (DCFDA), can be used to treat cells and react with the ROS for emitting fluorescent light. Accordingly, the amount of the ROS can be evaluated through the fluorescence.

Figure 10:
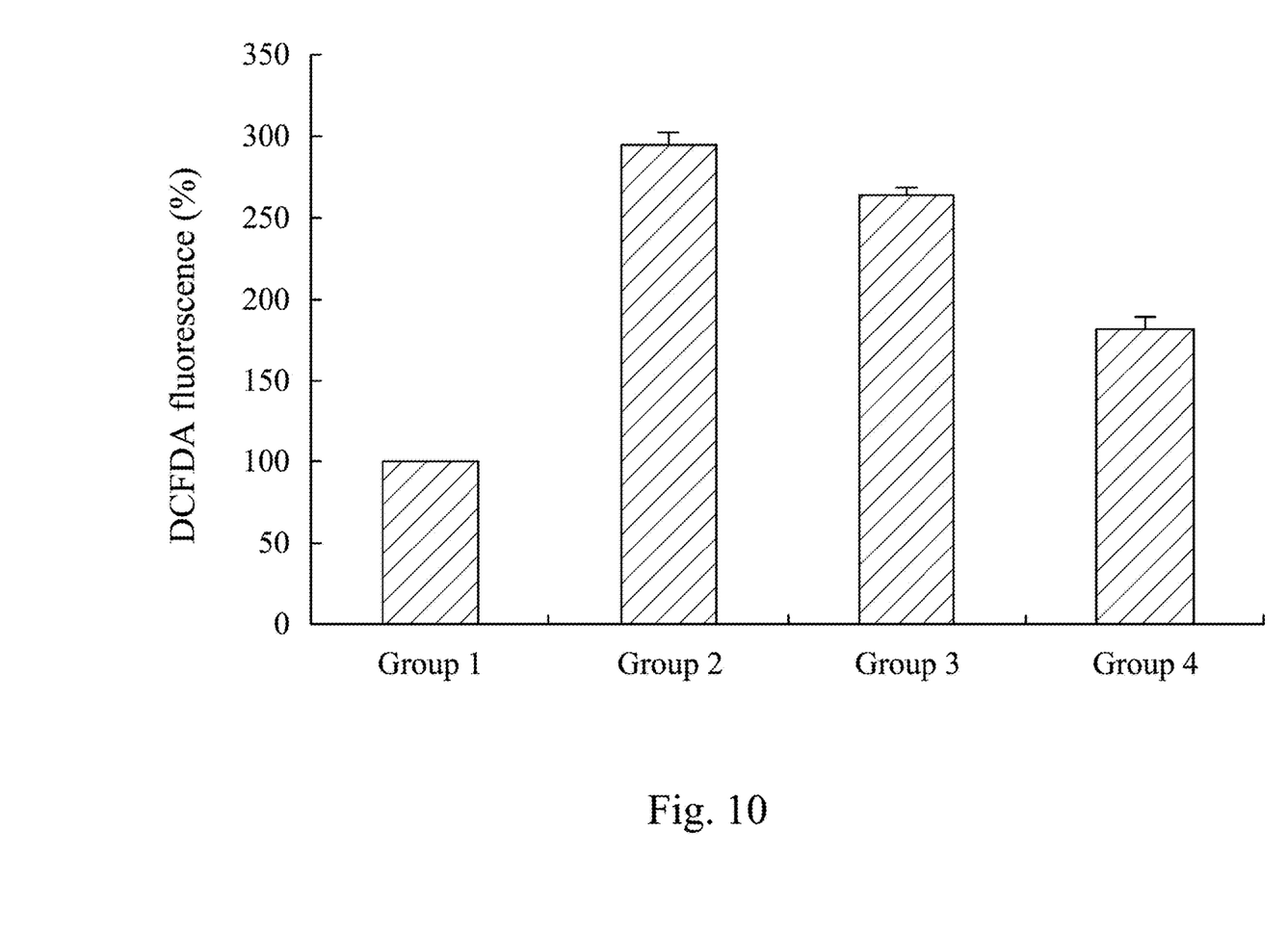
FIG. 10 is a result showing an effect of using the sustained-release composition of the 2nd embodiment to scavenge ROS.

In details, the in vitro cell model is performed by four groups according to different conditions. Group 1 is negative control. Group 2 is positive control, which only utilizes the lipopolysaccharide to stimulate the macrophage. In Group 3, the poly lactic-co-glycolic acid microspheres, which do not carry the magnesium, are used to treat the lipopolysaccharide-activated macrophage. In Group 4, the sustained-release compositions of the 2nd embodiment of the present disclosure are used to treat the lipopolysaccharide-activated. Please refer to FIG. 10, which is a result showing an effect of using the sustained-release composition of the 2nd embodiment to scavenge ROS. As shown in FIG. 10, the sustained-release composition of the 2nd embodiment can release the hydrogen slowly and continuously to allow the hydrogen to react with the ROS, such as hydroxyl radicals, so as to scavenge the ROS. Thus, the fluorescence of Group 4 is lowest. That is, the sustained-release composition of the present disclosure can scavenge the reactive species efficiently so as to prevent the tissues from the damage resulted from the oxidative stress.

To sum up, the sustained-release composition utilizes the carrier for carrying the precursor so as to produce the therapeutic gas slowly and continuously for treat indications for hydrogen sulfide therapy or hydrogen therapy effectively. Thus, a long-term therapeutic effect can be achieved by the present disclosure.

Although the present disclosure has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A sustained-release composition for producing a therapeutic gas, consisting of:
   a precursor being diallyl trisulfide; and
   a carrier for carrying the precursor with an efficient amount, wherein the carrier comprises a poly lactic-co-glycolic acid copolymer;
   wherein the sustained-release composition is a microsphere with an average particle size ranging from 0.2 μm to 300 μm.

2. The sustained-release composition of claim 1, wherein a copolymerization ratio of polylactic acid in the poly lactic-co-glycolic acid copolymer ranges from 50 wt % to 80 wt %, and a copolymerization ratio of polyglycolic acid in the poly lactic-co-glycolic acid copolymer ranges from 20 wt % to 50 wt %.

3. The sustained-release composition of claim 1, wherein the sustained-release composition contains 1 wt % to 30 wt % of the diallyl trisulfide based on the total weight of the sustained-release composition.

4. A method for fabricating the sustained-release composition of claim 1, comprising:
   providing a first solution as an oil phase, wherein the first solution comprises the poly lactic-co-glycolic acid copolymer, the precursor and a solvent;
   providing a second solution as a water phase;
   performing a single emulsification by mixing the first solution and the second solution for forming the sustained-release composition; and
   collecting the sustained-release composition.

5. The method of claim 4, wherein a copolymerization ratio of polylactic acid in the poly lactic-co-glycolic acid copolymer ranges from 50 wt % to 80 wt %, and a copolymerization ratio of polyglycolic acid in the poly lactic-co-glycolic acid copolymer ranges from 20 wt % to 50 wt %.

6. The method of claim 4, wherein a mixing ratio of a volume of the first solution to a volume of the second solution ranges from 1:1 to 1:12 in the step of performing the single emulsification.

7. The method of claim 4, wherein the solvent provided in the step of providing the first solution is dichloromethane, trichloromethane or ethyl acetate.

8. The method of claim 4, wherein the second solution is a solution containing polyvinyl alcohol, sodium lauryl sulfate, dimethylaminoborane, or a polyoxyethylene-polyoxypropylene block copolymer.

9. A method for treating indications for hydrogen sulfide therapy or hydrogen therapy, comprising:
   administering an effective amount of the sustained-release composition of claim 1 to a subject suffered from the indications for hydrogen sulfide therapy.

10. The method of claim 9, wherein a copolymerization ratio of polylactic acid in the poly lactic-co-glycolic acid copolymer ranges from 50 wt % to 80 wt %, and a copolymerization ratio of polyglycolic acid in the poly lactic-co-glycolic acid copolymer ranges from 20 wt % to 50 wt %.

* * * * *